United States Patent [19]

König et al.

[11] Patent Number: 4,487,764

[45] Date of Patent: Dec. 11, 1984

[54] NEW PEPTIDES AND A PROCESS FOR THEIR PREPARATION

[75] Inventors: Wolfgang König, Hofheim am Taunus; Rolf Geiger, Frankfurt am Main; Rainer Obermeier, Hattersheim am Main; Hubert Müllner, Kelkheim, all of Fed. Rep. of Germany

[73] Assignee: Hoechst Aktiengesellschaft, Frankfurt am Main, Fed. Rep. of Germany

[21] Appl. No.: 443,900

[22] Filed: Nov. 23, 1982

[30] Foreign Application Priority Data

Nov. 25, 1981 [DE] Fed. Rep. of Germany ....... 3146598

[51] Int. Cl.$^3$ .................... A61K 37/00; C07C 103/52
[52] U.S. Cl. .............................. 424/177; 260/112.5 R
[58] Field of Search .................. 260/112.5 R; 424/177

[56] References Cited

U.S. PATENT DOCUMENTS 4,001,199  1/1977  Fujino et al. ............... 260/112.5 R
4,073,890  2/1978  Fujino et al. ............... 260/112.5 R
4,309,340  1/1982  Sarantakis ................... 260/112.5 R
4,420,424 12/1983  Geiger et al. ............... 260/112.5 R

FOREIGN PATENT DOCUMENTS 0025897 1/1981 European Pat. Off. ..... 260/112.5 R
0037246 7/1981 European Pat. Off. ..... 260/112.5 R
1596535 8/1981 United Kingdom .

OTHER PUBLICATIONS

Chem. Abstr. 97, 56235a, (1982).
"Organic Chemistry", Morrison et al., Allyn and Bacon, Inc., Boston, 1966, p. 1099.

Primary Examiner—Delbert R. Phillips
Attorney, Agent, or Firm—Curtis, Morris & Safford

[57] ABSTRACT

A peptide of the formula $$B_1-B_2-A_1-A_2-X$$

in which
$B_1$ denotes a basic aminoacid,
$B_2$ denotes a basic aminoacid,
$A_1$ denotes an aromatic aminoacid,
$A_2$ denotes an aromatic aminoacid and
X denotes an aminoacid in which the carboxyl group can be esterified, a process for the preparation thereof and the use thereof.

10 Claims, No Drawings

NEW PEPTIDES AND A PROCESS FOR THEIR PREPARATION

Several peptides (for example thymosin-$\alpha_1$ and thymopoietin II) which are instrumental in differentiating ("maturing") thymus-dependent lymphocytes (T-cells), have been isolated from thymus extracts. A part sequence of thymopoietin II, Arg-Lys-Asp-Val-Tyr, also exhibits an action similar to that of thymopoietin in the corresponding test systems, for example the rosette test (Science (1979) 204, 1309 - 1310).

The said rosette test and also the PHA-stimulation test are suitable for investigating the effect of smaller peptides on lymphocytes.

In the rosette test, the maturation of lymphocytes from human umbilical cord blood is followed by rosetting with sheep erythrocytes under cold conditions. This test is specific for T-cells, i.e. it makes it possible to observe the displacement of $R^-$-T-cells into $R^+$-T-cells. Umbilical cord blood contains a relatively large number of immature or incompletely differentiated lymphocytes, so that the base value (standard value) of rosette-forming T-cells is lower than that of lymphocytes of the peripheral blood of adults.

A low rosette number can be correlated with a low immunity status on the basis of investigations carried out on the blood of patients suffering from auto-immunity diseases or tumors. In the test, a count and comparison are made of the numbers of rosettes of lymphocyteerythrocyte systems which have been pre-incubated either only in a nutrient medium without additives or in the nutrient medium to which the substance to be tested has been added.

The concentration of the peptides investigated is varied in this test between about 10 ng/ml and 1 μg/ml, 5 μg/ml, 10 μg/ml. The evaluation only includes rosettes consisting of at least one lymphocyte and three adhering erythrocytes.

In the PHA-stimulation test (PHA=phythemagglutinin) or lymphocyte transformation test, inferences are drawn as to the number of ripe, i.e. stimulatable, lymphocytes, not via investigation of the surface antigens, but by the functional test for stimulatability using the plant lectin PHA. The lymphocytes (T-cells) are stimulated by the lectin, in a manner similar to that caused by bacterial or viral antigens, to produce a blast transformation. This leads to a proliferation either directly or through the secretion of lymphokines. The incorporation of radioactive thymidine within a specific time is then a measure of the number of stimulated cells. Only the mature or immunologically potent T-cells are stimulated. The effect of a substance on the maturation of lymphocytes can therefore be followed by means of this test. However, the stimulation must be suboptimal, since at higher concentrations other subpopulations of lymphocytes are also stimulated and the effect can no longer be observed. The peptides to be investigated had been added to the culture medium in various concentrations. They are present during the whole duration of the test (up to 72 hours).

No account is taken in these investigations of a possible degradation of the peptides caused by serum or lymphocyte proteases.

Peptides have now been found, the action of which exceeds that of the known peptide Arg-Lys-Asp-Val-Tyr, particularly in the specific PHA test. These new peptides can be characterized as follows, in accordance with the general properties of their members: basic-basic-aromatic-aromatic-optional.

The invention relates, accordingly, to peptides of the general formula $$B_1-B_2-A_1-A_2-X,$$

in which:

$B_1$ denotes a basic aminoacid, preferably arginine or lysine, in each case in the L-or D-configuration, it being possible, if appropriate, for the α-amino group to be acylated, $B_2$ denotes a basic aminoacid, preferably arginine or lysine, $A_1$ denotes an aromatic aminoacid, preferably phenylalanine, tyrosine or tryptophan, in each case in the L- or D-configuration, $A_2$ denotes an aromatic aminoacid, preferably phenylanine, tyrosine or tryptophan and X denotes any desired aminoacid, preferably proline, glycine or arginine, it being possible for the carboxyl group to be esterified, preferably with an aliphatic alcohol having 1-6 carbon atoms.

The substituent (protective group) on the α-amino group of $B_1$, and the aminoacid X are not critical for the action of the peptides according to the invention. They can, however, be of importance for their stability and bio-availability and can thus be important in a quantitative respect.

Protective groups of the urethane type are particularly advantageous in this respect, since they protect the peptides against an N-terminal degradation caused by acylases and aminopeptidases. The urethane protective groups which are customary in peptide chemistry, such as benzyloxycarbonyl or tert.-butoxycarbonyl, are particularly suitable. Simple alkyloxycarbonyl groups also serve this purpose, however. Normal acyl groups, which, like acetyl, are admittedly capable of protecting the peptide against aminopeptidases, but not against acylases, are less advantageous.

X can represent any desired α-aminoacid, including an α-aminoacid which is substituted on side chain groups. For example, only quantitative differences exist between Gly, Arg or proline as X. Peptides which prove particularly effective are those in which X represents a basic aminoacid, such as arginine. Esterification of the carboxyl group with an aliphatic alcohol, such as methanol, ethanol or a higher alcohol, for example n-hexanol, can also be advantageous for the action and bio-availability of the peptide.

The invention also relates to a process for the preparation of the said peptides. The process comprises synthesizing sequences of aminoacids of the formula $$B_1-B_2-A_1-A_2-X$$

by methods of peptide chemistry.

The synthesis of the compounds according to the invention follows the known methods of peptide chemistry, such as are described in detail, for example, in Houben-Weyl, Methoden der Organischen Chemie ("Methods of Organic Chemistry"), volume 15. The examples quoted on the following pages illustrate the methods of synthesis which are known per se.

The compounds according to the invention can be used for the treatment of deficiencies of immunity, viral and fungoid infections and also chronic bacterial infections, and autoimmunity diseases, and for the therapy of diseases caused by cells having immunologically relevant alterations in the characteristics of the cell membrane (for example tumor cells).

The compound (V) Arg-Lys-Asp-Val-Tyr-OH was used as a known comparison substance. Results of the PHA stimulation test:

| Test substance | Concentration µg/ml | PHA concentration µg/ml | Incorporation of 3H—thymidine (cpm) | Stimulation index SI | X ± SEM |
|---|---|---|---|---|---|
| V | 1 | 10 | 59073 to 61624 | 1.06 | |
|   |   | 8  | 46392 to 58607 | 1.26 | 1.17 ± 0.06 |
|   |   | 4  | 26875 to 32247 | 1.20 | |
| A | 1 | 10 | 14356 to 18388 | 1.28 | |
|   |   | 8  | 11517 to 14031 | 1.22 | 1.32 ± 0.07 |
|   |   | 4  | 2727 to 3947   | 1.45 | |
| B | 1 | 10 | 19848 to 25888 | 1.30 | |
|   |   | 8  | 5300 to 5801   | 1.09 | 1.16 ± 0.05 |
|   |   | 4  | 5499 to 6073   | 1.10 | |
| D | 1 | 10 | 5038 to 8713   | 1.73 | |
|   |   | 8  | 5185 to 5924   | 1.14 | 1.33 ± 0.2 |
|   |   | 4  | 4415 to 4999   | 1.13 | |
| E | 1 | 10 | 12650 to 15231 | 1.20 | |
|   |   | 8  | 12693 to 13148 | 1.12 | 1.12 ± 0.05 |
|   |   | 4  | 8105 to 9072   | 1.12 | |

The invention also relates, in this respect, to the use of the said peptides quite generally for influencing the maturation of T-lymphocytes, and to an agent containing the peptides as the active compound.

The administration of the peptides according to the invention can be effected intravenously, subcutaneously or intranasally.

For an adult of normal body weight the dosage is 0.1–50 µg, preferably 1.5–7.5 µg per individual dose when administered parenterally, and 1–500 µg, preferably 15–75 µg, when administered intranasally. In severe cases, they can also be increased, since toxic properties have not hitherto been observed. It is also possible to reduce the dose.

The compounds according to the invention can be administered intranasally or parenterally in an appropriate pharmaceutical preparation. For an intranasal administration form, the active compounds are mixed with the additives customary for this purpose, such as stabilizers or inert diluents, and are converted by customary methods into suitable administration forms, such as aqueous, alcoholic or oily suspensions or aqueous, alcoholic or oily solutions. Examples of suitable oily excipients or solvents are vegetable or animal oils, such as sunflower oil or fish-liver oil.

For subcutaneous or intravenous administration, the active compounds or physiologically acceptable salts thereof are converted into solutions, suspensions or emulsions, if desired together with the substances customary for this purpose, such as solubilizers, emulsifiers or further auxiliaries. Examples of suitable solvents for the new active compounds and the corresponding physiologically acceptable salts are: water, physiological sodium chloride solutions or alcohols, for example ethanol, propanediol or glycerol, in addition also sugar solutions, such as glucose or mannitol solutions, or a mixture of the various solvents mentioned.

The activity of the compounds is demonstrated by the pharmacological data following.

The following compounds were investigated in the PHA test:
(A) Lys-Arg-Tyr-Tyr-Gly-OEt.
(B) Lys-Lys-Tyr-Phe-Arg-OH
(D) D-Lys-Arg-D-Phe-Trp-Pro-OH
(E) Arg-Lys-Tyr-Phe-Gln-OH The following examples illustrate the invention, in particular the synthesis of the peptides according to the invention.

The abbreviations used by IUPAC are generally employed.
Boc: tert.-butoxycarbonyl
Bu$^t$: tert.-butyl
DCC: dicyclohexylcarbodiimide
Et: ethyl
HOBt: 1-hydroxybenzotriazole
HOObt: 3-hydroxy-4-oxo-3,4-dihydro-1,2,3-benzotriazine
Mbh: 4,4'-dimethoxybenzohydryl
Me: methyl
Z: benzyloxycarbonyl

EXAMPLE 1

H-Lys-Arg-Tyr-Tyr-Gly-OEt diacetate (a) Z-Tyr(Bu$^t$)-Gly-OEt 6.4 ml (50 mmoles) of N-ethylmorpholine and 11.33 g (55 mmoles) of DCC are added at 0° C. and while stirring to a solution of 18.55 g (50 mmoles) of Z-Tyr(Bu$^t$)-OH, 6.98 g (50 mmoles) of H-Gly-OEt.HCl and 6.75 g (50 mmoles) of HOBt in 75 ml of dimethylformamide. The mixture is stirred for 2 hours at 0° C. and is allowed to stand overnight at room temperature. The precipitate is filtered off and the filtrate is concentrated in a high vacuum. The residue is partitioned between ethyl acetate and water. The ethyl acetate phase is extracted by shaking with NaHCO$_3$ solution, a KHSO$_4$/K$_2$SO$_4$ buffer and water, and is dried over Na$_2$SO$_4$ and concentrated. The residue is dissolved in diisopropyl ether. Undissolved material is filtered off and petroleum ether is added to the filtrate. The mixture is cooled for a few hours in an ice bath and the precipitate is filtered off. Yield 20.63 g (89%), melting point 108° C. $[\alpha]_D^{22} = -13.4°$ (c=1, methanol).

(b) H-Tyr(Bu$^t$)-Gly-OEt.HCl 19.78 g (43 mmoles) of Z-Tyr(Bu$^t$)-Gly-OEt are dissolved in 200 ml of methanol. A Pd-on-charcoal catalyst is added to this solution and hydrogen is passed through the solution while stirring and adding approx. 2N methanolic HCL at pH 4.5 (autotitrator), until no further methanolic HCl is taken up. The catalyst is then filtered off and the filtrate is concentrated. The residue is stirred with ether and suction-drained. Yield 14.87 g (93.7%), melting point 140°–142°, $[\alpha]_D^{22} = +30.9°$ (c=1, methanol).

(c) Z-Tyr(Bu$^t$)-Tyr(Bu$^t$)-Gly-OEt 5.12 ml (40 mmoles) of N-ethylmorpholine and 8.65 g (42 mmoles) of DCC are added at 0° C. to a solution of 14.35 g (40 mmoles) of H-Tyr(Bu$^t$)-Gly-OEt.HCl, 14.84 g (40 mmoles) of Z-Tyr(Bu$^t$)-OH and 5.4 g (40 mmoles) of HOBt in 100 ml of dimethylformamide. The mixture is worked up as in Example 1 a. The residue is triturated with petroleum ether. Yield 26.3 g. The substance is purified by chromatographing a solution in 9:1 methylene chloride/acetone over 150 g of silica gel. The fractions were concentrated and the residue triturated with ether. Yield 19.74 g (73%), melting point 113°, $[\alpha]_D^{22} = -28.7°$ (c=1, methanol).

(d) H-Tyr(Bu$^t$)-Tyr(Bu$^t$)-Gly-OEt.HCl 18.9 g (28 mmoles) of Z-Tyr(But)-Tyr(But)-Gly-OEt are dissolved in 200 ml of methanol and subjected to catalytic hydrogenation analogously to Example 1 b. The residue is triturated with a mixture of 250 ml of ether and 250 ml of petroleum ether and suction-drained. Yield 15.65 g (96%), $[\alpha]_D^{22} = +7.7°$ (c=1, methanol).

(e) Z-Arg(Z$_2$)-Tyr(Bu$^t$)-Tyr(Bu$^t$)-Gly-OEt 1.28 ml (10 mmoles) of N-ethylmorpholine and 8.15 g (10.5 mmoles) of Z-Arg(Z$_2$)-OTcp are added to a solution of 5.78 g (10 mmoles) of H-Tyr(Bu$^t$)-Tyr(Bu$^t$)-Gly-OEt.HCl and 1.35 g (10 mmoles) of HOBt in 30 ml of dimethylformamide. The mixture is stirred for 4 hours at room temperature and left to stand overnight at room temperature, and the resulting gelatinous mass is stirred with 250 ml of water. The precipitate is filtered off and stirred successively with KHSO$_4$/K$_2$SO$_4$ buffer, in NaHCO$_3$ solution and water, and is suction-drained. Yield 10.47 g (95%), melting point 163°–165°, $[\alpha]_D^{23} = -16.1°$ (c=1, dimethylformamide).

(f) H-Arg-Tyr(Bu$^t$)-Tyr(Bu$^t$)-Gly-OEt.2 HCl 9.9 g (9 mmoles) of Z-Arg(Z$_2$)-Tyr(Bu$^t$)-Tyr-(Bu$^t$)-Gly-OEt are suspended in 300 ml of methanol and subjected to catalytic hydrogenation analogously to Example 1 b. The residue is triturated with ether. Yield 6.22 g (92%), melting point 76°–83°, $[\alpha]_D^{23} = +16.6°$ (c=1, methanol).

(g) Z-Lys(Boc)-Arg-Tyr(Bu$^t$)-Tyr(Bu$^t$)-Gly-OEt 1.03 g of N-ethylmorpholine and 4.76 g (8.5 mmoles) of Z-Lys(Boc)-OTcp are added to a soution of 5.98 g (8 mmoles) of H-Arg-Tyr(Bu$^t$)-Tyr(Bu$^t$)-Gly-OEt.2 HCl and 1.08 g (8 mmoles) of HOBt in 40 ml of dimethylformamide. The mixture is stirred for 6 hours at room temperature and left to stand overnight at room temperature. The mixture is worked up analogously to Example 1 a, but without extracting by shaking with acid. The residue is triturated with ether and purified further by being chromatographed in 9:1 methylene chloride/methanol over 100 g of silica gel. The appropriate fractions are concentrated and the residue is triturated with ether. Yield 5.88 g (72%), melting point 96°–99°, $[\alpha]_D^{25} = -22°$ (c=1, dimethylformamide).

(h) H-Lys-Arg-Tyr-Tyr-Gly-OEt diacetate 5.0 g (5 mmoles) of Z-Lys(Boc)-Arg-Tyr(Bu$^t$)-Tyr-(Bu$^t$)-Gly-OEt are dissolved in 50 ml 90% strength trifluoroacetic acid. The mixture is left to stand at room temperature for 2 hours and is concentrated. The residue is first triturated with ether and suction-drained. It is then triturated with water and suction-drained.

The substance (=Z-Lys-Arg-Tyr-Try-Gly-OEt trifluoroacetate) is then dissolved in 60 ml of 90% strength acetic acid and, after adding a Pd-on-charcoal catalyst, is subjected to catalytic hydrogenation by passing hydrogen through the solution. When the hydrogenation is complete, the catalyst is filtered off and the filtrate is concentrated. The residue is chromatographed in water over a weakly basic ion exchanger (acetate form). The eluate is freeze-dried. Yield 3.365 g. 800 mg of the eluate are purified by being chromatographed in 90% strength methanol over a crosslinked, hydroxypropylated dextran gel. Yield 506 mg, $[\alpha]_D^{24} = -10.7°$ (c=1, methanol). Aminoacid analysis (hydrolysis in 6N HCl for 24 hours at 120°): Gly 1.0, Tyr 1.7, Lys 1.0 and Arg 0.9.

EXAMPLE 2

Z-Lys-Lys-Tyr-Phe-Arg-OH diacetate

(a) Z-Tyr(Bu$^t$)-Phe-OMe 13 ml of N-ethylmorpholine and 22 g of DCC are added at 0° C. to a solution of 40.7 g (0.1 mmole) of Z-Tyr(Bu$^t$)-OH, 21.6 g of H-Phe-OMe hydrochloride and 13.5 g (0.1 mmole) of HOBt in 200 ml of dimethylformamide. The mixture is worked up as in the case of Example 1 a. The residue is triturated with petroleum ether and suction-drained. Yield 50.3 g (94%), melting point 103°–104° C., $[\alpha]_D^{24} = -12.3°$ (c=1, methanol).

(b) H-Tyr(Bu$^t$)-Phe-OMe.HCl 49.5 g of Z-Tyr(Bu$^t$)-Phe-OMe are dissolved in 800 ml of methanol and subjected to catalytic hydrogenation analogously to Example 1 b. The residue cannot be crystallized. Yield 43 g of an oil.

(c) Z-Lys(Boc)-Tyr(Bu$^t$)-Phe-OMe 6.43 ml of N-ethylmorpholine and 27.67 g of Z-Lys(-Boc)-OTcp are added to a solution of 21.5 g of H-Tyr(-Bu$^t$)-Phe-OMe.HCl and 6.67 g of HOBt in 150 ml of dimethylformamide. The mixture is stirred for 3 hours at room temperature and is concentrated. The residue is worked up analogously to Example 1 a. The substance is crystallized from ethyl acetate/petroleum ether. Yield 29.1 g (77%), melting point 93°–94°, $[\alpha]_D^{24} = -19.2°$ (C=1, methanol).

(d) H-Lys(Boc)-Tyr(Bu$^t$)-Phe-OMe.HCl 28 g of Z-Lys(Boc)-Tyr(Bu$^t$)-Phe-OMe are dissolved in 300 ml of methanol and subjected to catalytic hydrogenation analogously to Example 1 b. The residue crystallizes from ether. Yield 22.4 g (91.8%), melting point 145°–147°, $[\alpha]_D^{24} = +18.2°$ (c=1, methanol).

(e) Z-Lys(Boc)-Lys(Boc)-Tyr(Bu$^t$)-Phe-OMe 4.3 ml of N-ethylmorpholine and 18.48 g of Z-Lys(-Boc)-OTcp are added to a solution of 21.9 g of H-Lys(-Boc)-Tyr(Bu$^t$)-Phe-Ome.HCl and 4.46 g of HOBt in 130 ml of dimethylformamide. The mixture is stirred for 3 hours at room temperature. The peptide is then precipitated with 400 ml of water and 35 ml of saturated NaHCO$_3$ solution. The precipitate is filtered off. It is crystallized from ethyl acetate/petroleum ether. Yield 30.4 g (93%), melting point 159°–160°, $[\alpha]_D^{28} = -17.5°$ (c=1, methanol).

(f) Z-Lys(Boc)-Lys(Boc)-Tyr(Bu$^t$)-Phe-OH 20 g (approx. 20 mmoles) of Z-Lys(Boc)-Lys(Boc)-Tyr(Bu$^t$)-Phe-OBu$^t$ are dissolved almost completely in 100 ml of dioxane. 20 ml of 1N NaOH are added to the solution and the mixture is stirred for 1 hour at room temperature. Insoluble matter is then filtered off and 500 ml of ice water and 20 ml of 1N HCl are added to the filtrate. The precipitate is filtered off and dried. Yield 18.5 g. Thin layer chromatography in 8:2 methylene chloride/acetone showed that the saponification had not taken place completely. The substance still contains fairly large quantities of starting material. About 3 g of pure saponification product were isolated from the mixture by fractional crystallization from ethyl acetate. Melting point 156°–158°, $[\alpha]_D^{25} = -13.1°$ (c=1, methanol).

(g) Z-Lys(Boc)-Lys(Boc)-Tyr(Bu$^t$)-Phe-Arg-OBu$^t$ 0.26 ml of N-ethylmorpholine and 440 mg of DCC are added at 0° C. to a solution of 1.95 g (2 mmoles) of Z-Lys(Boc)-Lys(Boc)-Tyr(Bu$^t$)-Phe-OH, 606 mg (2 mmoles) of H-Arg-OBu$^t$.HCl and 326 mg (2 mmoles) of HOObt in 5 ml of dimethylacetamide. The mixture is first stirred for 2 hours at 0° C. and is left to stand overnight at room temperature. On the following day the precipitate is filtered off and the filtrate is concentrated. Yield 2.5 g. The substance is purified by being recrystallized twice from ethyl acetate. Yield 1.7 g, melting point 134°–137°, $[\alpha]_D^{26} = -26.4°$ (c=1, methanol).

(h) Z-Lys-Lys-Tyr-Phe-Arg-OH diacetate 1.6 g of Z-Lys(Boc)-Lys(Boc)-Tyr(Bu$^t$)-Phe-Arg-OBu$^t$ are dissolved in 15 ml of 90% strength trifluoroacetic acid. The solution is left to stand at room temperature for 1 hour and is concentrated. The residue is triturated with ether and is suction-drained. The residue is then dissolved in water and chromatographed over a weakly basic ion exchanger (acetate form). The eluate is concentrated and chromatographed in 90% strength methanol over a crosslinked, hydroxypropylated dextran gel. Yield 920 mg, $[\alpha]_D^{24} = -29.7°$ (c=1, methanol).

EXAMPLE 3

H-Lys-Lys-Tyr-Phe-Arg-OH diacetate 500 mg of Z-Lys-Lys-Tyr-Phe-Arg diacetate are dissolved in 20 ml of 90% strength acetic acid and subjected to catalytic hydrogenation analogously to Example 1 h. The residue is chromatographed in 90% strength methanol over a crosslinked, hydroxypropylated dextran gel. The eluate containing the peptide is concentrated and the residue is dissolved in water and freeze-dried. Yield 244 mg. Aminoacid analysis (hydrolysis in 6N HCl for 24 hours at 120° C.): Tyr 0.93, Phe 1.0, Lys 2.06 and Arg 0.9.

EXAMPLE 4

Z-D-Lys-Arg-D-Phe-Trp-Pro-Oh

(a) Z-Trp-Pro-OBu$^t$ 10.92 g (53 mmoles) of DCC are added at 0° C. to a solution of 16.9 g (50 mmoles) of Z-Trp-OH, 8.55 g (50 mmoles) of H-Pro-OBu$^t$ and 6.75 g (50 mmoles) of HOBt in 75 ml of dimethylformamide. The mixture is stirred for 2 hours at 0° C. and left to stand overnight at room temperature. The precipitate is filtered off and the filtrate is concentrated. The residue is worked up analogously to Example 1 a. The residue is triturated with ether. Yield 19.49 g (79%), melting point 173°, $[\alpha]_D^{25} = -54.2°$ (c=1, dimethylformamide).

(b) H-Trp-Pro-OBu$^t$.HCl 16.64 g (40 mmoles) of Z-Trp-Pro-OBu$^t$ in 200 ml of methanol are subjected to catalytic hydrogenation analogously to Example 1 b. The residue is triturated with ether. Yield 14.37 g, melting point 190°–195°, $[\alpha]_D^{25} = -22.4°$ (c=1, methanol).

(c) Z-D-Phe-Trp-Pro-OBu$^t$ 1.28 ml (10 mmoles) of N-ethylmorpholine and 2.26 g (11 mmoles) of DCC are added at 0° C. to a solution of 3.46 g (10 mmoles) of H-Trp-Pro-OBu$^t$.HCl. 2.29 g (10 mmoles) of Z-D-Phe-OH and 1.35 g (10 mmoles) of HOBt in 25 ml of dimethylformamide. The mixture is stirred for 2 hours at 0° C. and left to stand overnight at room temperature. The precipitate is filtered and the filtrate is concentrated. The residue is worked up analogously to Example 1 a. The residue crystallizes from ether. Yield 3.91 g (61%), melting point 186°, $[\alpha]_D^{23} = -53.6°$ (c=1, methanol).

Further peptide can be precipitated from the mother liquor by adding petroleum ether. Yield 0.85 g, melting point 183°.

(d) H-D-Phe-Trp-Pro-OBu$^t$.HCl 3.7 g of Z-D-Phe-Trp-Pro-OBu$^t$ in 100 ml of methanol are subjected to catalytic hydrogenation analogously to Example 1 b. The residue is triturated with ether. Yield 2.67 g, melting point 155°–165°, $[\alpha]_D^{23} = -75.8°$ (c=1, methanol).

(e) A-Arg(Z$_2$)-D-Phe-Trp-Pro-OBu$^t$ 0.58 ml (4.5 mmoles) of N-ethylmorpholine and 3.5 g (4.6 mmoles) of Z-Arg(Z$_2$)-OTcp are added at 0° C. to a solution of 2.43 g (4.5 mmoles) of H-D-Phe-Trp-Pro-OBu$^t$.HCl and 0.61 g (4.5 mmoles) of HOBt in 20 ml of dimethylformamide. The mixture is stirred for 6 hours at room temperature and left to stand overnight at room temperature. The mixture is concentrated and worked up analogously to Example 1 a. The residue is triturated with ether. Yield 4.01 g. Recrystallization from 25 ml of 94% strength alcohol gives 3.58 g (75%), melting point 142°–145°, $[\alpha]_D^{23} = -19.2°$ (c=1, methanol).

(f) H-Arg-D-Phe-Trp-Pro-OBu$^t$.2 HCl 3 g of Z-Arg(Z$_2$)-D-Phe-Trp-Pro-OBu$^t$ are suspended in 100 ml of methanol and subjected to catalytic hydrogenation analogously to Example 1 b. The residue is triturated with ether. Yield 2.01 g (97%), melting point 190°–200°, $[\alpha]_D^{23} = -27.0°$ (c=1, methanol).

(g) Z-D-Lys(Boc)-Arg-D-Phe-Trp-Pro-OBu$^t$ 0.26 ml (2 mmoles) of N-ethylmorpholine and 1.23 g (1.2 mmoles) of Z-D-Lys(Boc)-OTcp are added at 0° C. to a solution of 1.47 g (2 mmoles) of H-Arg-D-Phe-Trp-Pro-Obu$^t$.2 HCl and 0.27 g (2 mmoles) of HOBt in 10 ml of dimethylformamide. The mixture is stirred for 4 hours at room temperature and is concentrated and the residue is partitioned between ethyl acetate and a saturated NaHCO$_3$ solution. The ethyl acetate phase is extracted by shaking with water, dried over Na$_2$SO$_4$ and concentrated. The residue is triturated with ether and suction-drained. Yield 1.65 g, melting point 125°–132°, $[\alpha]_D^{25} = -21.9°$ (c=1, methanol).

(h) Z-D-Lys-Arg-D-Phe-Trp-Pro-OH 1.55 g of Z-D-Lys(Boc)-Arg-D-Phe-Trp-Pro-OBu$^t$ are dissolved in 14.5 ml of 90 percent strength trifluoroacetic acid and 1.5 ml of ethyl mercaptan. The solution is left to stand for 1 hour at room temperature and is concentrated. The residue is dissolved in water and chromatographed over a weakly basic ion exchanger (acetate form). The eluate is freeze-dried. Yield 883 mg. The peptide is purified by being chromatographed in 90 percent strength methanol over a crosslinked, hydroxypropylated dextran gel. Yield 570 mg, $[\alpha]_D^{22} = -24.6°$ (c=1, methanol).

EXAMPLE 5

H-D-Lys-Arg-D-Phe-Trp-Pro-Oh triacetate 380 mg of Z-D-Lys-Arg-D-Phe-Trp-Pro-OH acetate are dissolved in 20 ml of 90 percent strength acetic acid and subjected to catalytic hydrogenation analogously to Example 1 h. The residue is chromatographed in 90 percent strength methanol over a crosslinked, hydroxypropylated dextran gel. Yield 140 mg, $[\alpha]_D^{23} = -26.8°$ (c=1, methanol).

Aminoacid analysis (hydrolysis in 6N HCl for 24 hours at 120°): Pro 0.95, Phe 1.0, Lys 1.03 and Arg 0.93; Trp is destroyed in the course of the hydrolysis, but could be detected by a UV spectrum.

EXAMPLE 6

H-Arg-Lys-Tyr-Phe-Gln-OH acetate

(a) H-Tyr(Bu$^t$)-Phe-Gln(Mbh)-OH acetate 30 g of Z-Tyr(Bu$^t$)-Phe-Gln(Mbh)-OH are dissolved in 600 ml of 90 percent strength acetic acid and subjected to catalytic hydrogenation analogously to Example 1 h. The residue is triturated with ether. Yield 24.2 g (88%), melting point 192°–193°, $[\alpha]_D^{24} = +16.9°$ (c=1, 80 percent strength acetic acid).

(b) Z-Lys(Boc)-Tyr(Bu$^t$)-Phe-Gln(Mbh)-OH 3.92 g of Z-Lys(Boc)-OTcp are added to a solution of 5.6 g of H-Tyr(Bu$^t$)-Phe-Gln(Mbh)-OH acetate and 0.95 g of HOBt in 20 ml of dimethylformamide. The mixture is stirred for 4 hours at room temperature and left to stand overnight at room temperature. On the following day the mixture is stirred with 100 ml of water and 7 ml of saturated NaHCO$_3$ solution. The precipitate is filtered off and dried. Yield 8.09 g (95%), melting point 177°–184°, $[\alpha]_D^{28} = -10.6°$ (c=1, 80 percent strength acetic acid).

(c) H-Lys(Boc)-Tyr(Bu$^t$)-Phe-Gln(Mbh)-OH acetate 7.5 g of Z-Lys(Boc)-Tyr(Bu$^t$)-Phe-Gln(Mbh)-OH are dissolved in 350 ml of 90 percent strength acetic acid and subjected to catalytic hydrogenation analogously to Example 1 h. The residue is triturated with ether and suction-drained. Yield 4.81 g (74%), melting point 136°–138°, $[\alpha]_D^{28} = +8.2°$ (c=1, 80 percent strength acetic acid).

(d) Z-Arg(Z$_2$)-Lys(Boc)-Tyr(Bu$^t$)-Phe-Gln(Mbh)-OH

A solution of 1.9 g of Z-Arg(Z$_2$)-OTcp in 5 ml of dimethylformamide is added to a solution of 2.57 g (2.5 mmoles) of H-Lys(Boc)-Tyr(Bu$^t$)-Phe-Gln(Mbh) acetate and 0.34 g of HOBt in 10 ml of dimethylformamide. The mixture is stirred for 5 hours at room temperature and left to stand overnight. The mixture is then stirred with 50 ml of water and 3.5 ml of saturated NaHCO$_3$ solution. The precipitate is filtered off, washed thoroughly and dried. Yield 3.75 g (98%), melting point 132°–140°, $[\alpha]_D^{24} = -19°$ (c=1, acetic acid).

(e) Z-Arg(Z$_2$)-Lys-Tyr-Phe-Gln-OH 3 g (2 mmoles) of Z-Arg(Z$_2$)-Lys(Boc)-Tyr(Bu$^t$)-Phe-Gln(Mbh)-OH are dissolved in 20 ml of 90 percent strength trifluoroacetic acid. The mixture is left to stand for 1 hour at room temperature and is concentrated and the residue is triturated with ether. Yield 2.11 g (92%), melting point 70°–78° (decomposition).

(f) H-Arg-Lys-Tyr-Phe-Gln-OH diacetate 2 g of Z-Arg(Z$_2$)-Lys-Tyr-Phe-Gln-OH are dissolved in 90 percent strength acetic acid and subjected to catalytic hydrogenation analogously to Example 1 h. The residue is chromatographed in 90 percent strength methanol over a crosslinked, hydroxypropylated dextran gel. Yield 473 mg, $[\alpha]_D^{21} = -7.4°$ (c=1, water), aminoacid analysis (hydrolysis in 6N HCl for 24 hours at 120°): Gln 1.0, Tyr 0.91, Phe 0.99, Lys 1.05 and Arg 0.94.

We claim:

1. A peptide of the formula

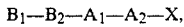

wherein
- B$_1$ is in the L- or D- configuration and is arginine, lysine, or lysine which is acylated by a protective group of the urethane type,
- B$_2$ is arginine or lysine,
- A$_1$ is in the L- or D- configuration and is phenylalanine, tyrosine, or tryptophan,
- A$_2$ is phenylalanine, tyrosine, or tryptophan, and
- X is glutamine, glycine, proline, or arginine, or is an ester of such an amino acid with an aliphatic alcohol having 1–6 carbon atoms.

2. A peptide as in claim 1 which is Lys - Arg - Tyr - Tyr - Gly - OEt.

3. A peptide as in claim 1 which is Lys - Lys - Tyr - Phe - Arg - OH.

4. A peptide as in claim 1 which is Z - Lys - Lys - Tyr - Phe - Arg - OH.

5. A peptide as in claim 1 which is D - Lys - Arg - D - Phe - Trp - Pro - OH.

6. A peptide as in claim 1 which is Z - D - Lys - Arg - D - Phe - Trp - Pro - OH.

7. A peptide as in claim 1 which is Arg - Lys - Tyr - Phe - Gln - OH.

8. The method for influencing the maturing of T-lymphocytes in vitro which comprises treating said lymphocytes with a peptide as in claim 7.

9. A method for treating deficiencies in the immune system in a patient suffering from such deficiencies, which method comprises administering to said patient an effective amount of a peptide as in claim 1.

10. A pharmaceutical composition for treatment of deficiencies of the immune system, which composition comprises an effective amount of a peptide as in claim 1 and a pharmaceutically acceptable carrier therefor.

* * * * *